United States Patent
Mitsuhashi et al.

(10) Patent No.: US 6,428,202 B1
(45) Date of Patent: Aug. 6, 2002

(54) METHOD FOR INSPECTING CONNECTION STATE OF ELECTRONIC PART AND A SUBSTRATE, AND APPARATUS FOR THE SAME

(75) Inventors: Hideo Mitsuhashi; Katsuhisa Ookawa, both of Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/523,000

(22) Filed: Mar. 9, 2000

(30) Foreign Application Priority Data

Mar. 12, 1999 (JP) .......................... 11-066786

(51) Int. Cl.[7] ............................. G01N 25/72
(52) U.S. Cl. ........................................ 374/5
(58) Field of Search ................ 374/4–6, 45, 57, 374/50, 126, 128

(56) References Cited

U.S. PATENT DOCUMENTS

| | | | |
|---|---|---|---|
| 4,484,820 A | * 11/1984 | Rosencwaig | 374/6 |
| 4,620,799 A | * 11/1986 | Palazzetti et al. | 374/5 |
| 4,956,538 A | * 9/1990 | Moslehi | 219/121.6 |
| 5,201,841 A | * 4/1993 | Lebeau et al. | 374/4 |
| 5,246,291 A | * 9/1993 | Lebeau et al. | 374/5 |
| 5,250,809 A | * 10/1993 | Nakata et al. | 250/330 |
| 5,407,275 A | * 4/1995 | Long | 374/45 |
| 5,493,594 A | * 2/1996 | Hamada et al. | 378/34 |
| 5,971,608 A | * 10/1999 | Koizumi | 374/5 |
| 5,990,553 A | * 11/1999 | Morita et al. | 257/729 |
| 6,028,358 A | * 2/2000 | Suzuki | 257/737 |

FOREIGN PATENT DOCUMENTS

| | | | | |
|---|---|---|---|---|
| GB | 2164147 A | * | 3/1986 | G01N/25/72 |
| JP | 0243574 | * | 12/1985 | 374/5 |
| JP | 06132586 A | * | 5/1994 | H01S/3/094 |

OTHER PUBLICATIONS

D.Schumacher. Measuring Microbond Integrity With an Infrared Microradiometer. 27th National Fall Conference of the American Society for Non–Destructive Testing. Oct., 1967.*

* cited by examiner

*Primary Examiner*—Diego Gutierrez
*Assistant Examiner*—Gail Verbitsky
(74) *Attorney, Agent, or Firm*—Whitham, Curtis & Christofferson, PC

(57) ABSTRACT

A method for inspecting a connection state of an electronic part and an apparatus for the same which permits judgement of the quality of the connection state at high accuracy without needing structural addition of through holes and pads for use in connection state inspection are provided. The has the steps of: heating a first specific position on the electronic part, measuring a temperature rise of a second specific position thermally coupled to the first specific position, and judging the quality of the connection state of the solder connecting portion by comparing the measured temperature rise and a reference temperature rise.

5 Claims, 9 Drawing Sheets

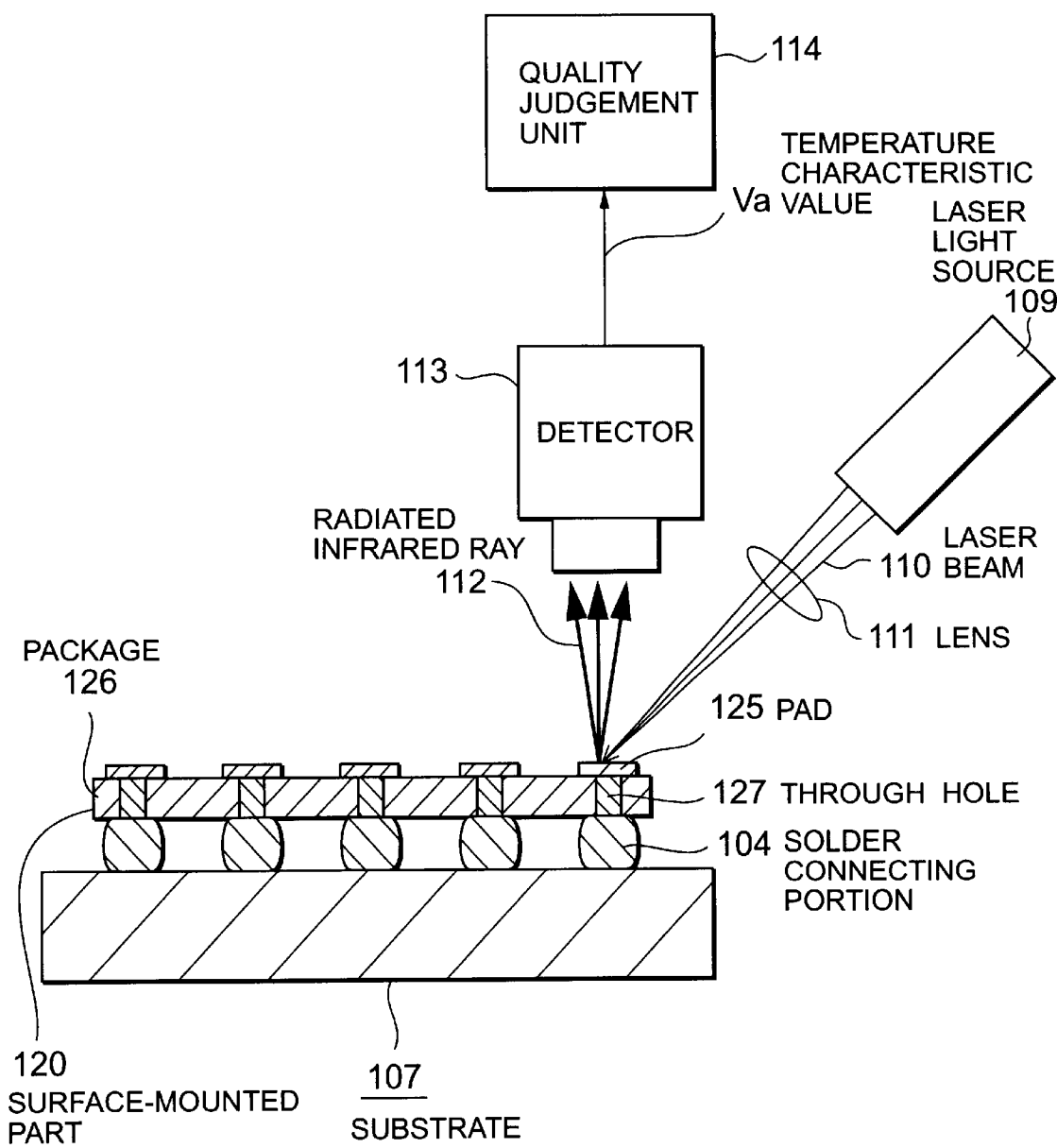

METHOD FOR INSPECTING CONNECTION STATE OF ELECTRONIC PART AND A SUBSTRATE, AND APPARATUS FOR THE SAME

BACKGROUND OF THE INVENTION

1. Field of the Invention

The present invention relates to a method for inspecting the connection state of an electronic part and the substrate, and an apparatus for the same.

2. Description of the Prior Art

As known inspection methods according to the prior for the state of connection between an electronic part and a substrate, an electrical continuity inspection, a visual inspection and an X-ray inspection are existing.

The Japanese Published Patent No. 38501/1995 (published on Apr. 26, 1995 in Japan) discloses a technique whereby the part to be checked is irradiated with laser light and its connection state is judged according to its temperature rise. This technique will be described below as an example of the prior art.

FIG. 9 is a front cross-sectional view of a connection state inspecting apparatus for an electronic part and a substrate according to the conventional example.

The conventional apparatus shown in FIG. 9 consists of a laser light source 109, a lens 111, a detector 113 and a quality judgement unit 114.

A surface-mounted part 120, which is to be checked by this apparatus, consists of a package 126, pads 125 formed over the top surface of this package 126, and through holes 127 electrically connected to these pads 125 and penetrating the package 126 downward. Each of the through holes 127 is connected to the upper surface of a substrate 107 by solder connecting portions 104.

In this apparatus according to the prior art, the pads 125 are irradiated with a laser beam 110, radiated infrared rays 112 from the pads 125 are received to measure the increment of a temperature character value Va. This increment is compared with a preset increment to evaluate the connection state of the solder connecting portions 104.

This conventional apparatus is characterized in that the pads 125 and the through holes 127 are structurally added afterward to the package 126 to heat the solder connecting portions 104 which are not exposed on the surface and accordingly cannot be irradiated with the laser beam 110. The solder connecting portions 104 are thermally coupled to the pads 125 by the through holes 127.

However, this conventional apparatus has the following problems.

First, the need to form the pads 125 and the through holes 127 within the package 126 for the sole purpose of inspecting the connection state significantly limits the arrangement of wiring routes in the package 126.

Second, a step to bore many through holes 127 into the package 126, a step to fill these through holes 127 with electroconductive material and a step to form a pad 125 over the top of each through hole 127 are indispensable merely for inspecting the connection state. This results in a substantial increase in the number of required steps in the manufacturing process and a corresponding increase in production cost.

Third, the low intensity of the radiated infrared rays 112 emitted by the temperature rise of the pads 125 brings down the accuracy of quality of judgement.

Thus, a plating layer of metal, such as nickel or gold, is usually formed over the surface of each of the pads 125. These metals have the extremely low infrared emission character of any such metal invites a very low intensity of the radiated infrared rays 112 emitted from the pads 125 themselves even if the temperature of the pads 125 rises.

Fourth, a high intensity of unnecessary infrared rays scattered over the surfaces of the pads 125 brings down the accuracy of quality judgement.

Because gold has very high infrared reflection character, the reflected light on the pads 125 is incident into the detector 113 as noise components.

SUMMARY OF THE INVENTION

In view of these problems, a first object of the present invention is to provide a method for inspecting the connection state of an electronic part and a substrate and an apparatus for the same which permits judgement of the quality of the connection state at high accuracy without needing structural addition of through holes and pads for use in connection state inspection.

A second object of the present invention is to provide a method for inspecting the connection state of an electronic part and a substrate and an apparatus for the same which permits judgement of the quality of the connection state at high accuracy even where the terminals for electrical inspection of the part to be inspected are gold-plated or otherwise and accordingly poor in infrared emission character.

A method for inspecting a connection state of an electronic part and a substrate, the electronic part having a terminal for electrical inspection electrically connected to a solder connecting portion, and being connected to a surface of the substrate by the solder connecting portion, has the steps of: heating a first specific position on the electronic part, measuring a temperature rise of a second specific position thermally coupled to the first specific position, and judging the quality of the connection state of the solder connecting portion by comparing the measured temperature rise and a reference temperature rise.

An apparatus for inspecting a connection state of an electronic part and a substrate, the electronic part having a terminal for electrical inspection electrically connected to solder connecting portion, and being connected to a surface of the substrate by the solder connecting portion, has: a heating unit for heating a first specific position on the electronic part, a thermometer for measuring a temperature rise of a second specific position thermally coupled to the first specific position, and a quality judgement unit for judging the connection state of the solder connecting portion by comparing the measured temperature rise with a reference temperature rise.

By the adoption of such the method and the apparatus, the invention makes possible to judge the connection state by using the terminals for electrical inspection, which are previously formed thereon.

Even where the infrared emission character of the terminals is low, the quality of the connection state can be judged on the basis of the temperature rise on specific positions thermally connected to these terminals.

BRIEF DESCRIPTION OF THE DRAWINGS

FIG. 9 is a front cross-sectional view of a connection state inspecting apparatus for an electronic part and a substrate according to the conventional example.

DETAILED DESCRIPTION OF THE PREFERRED EMBODIMENTS

First Embodiment

Figure 1:
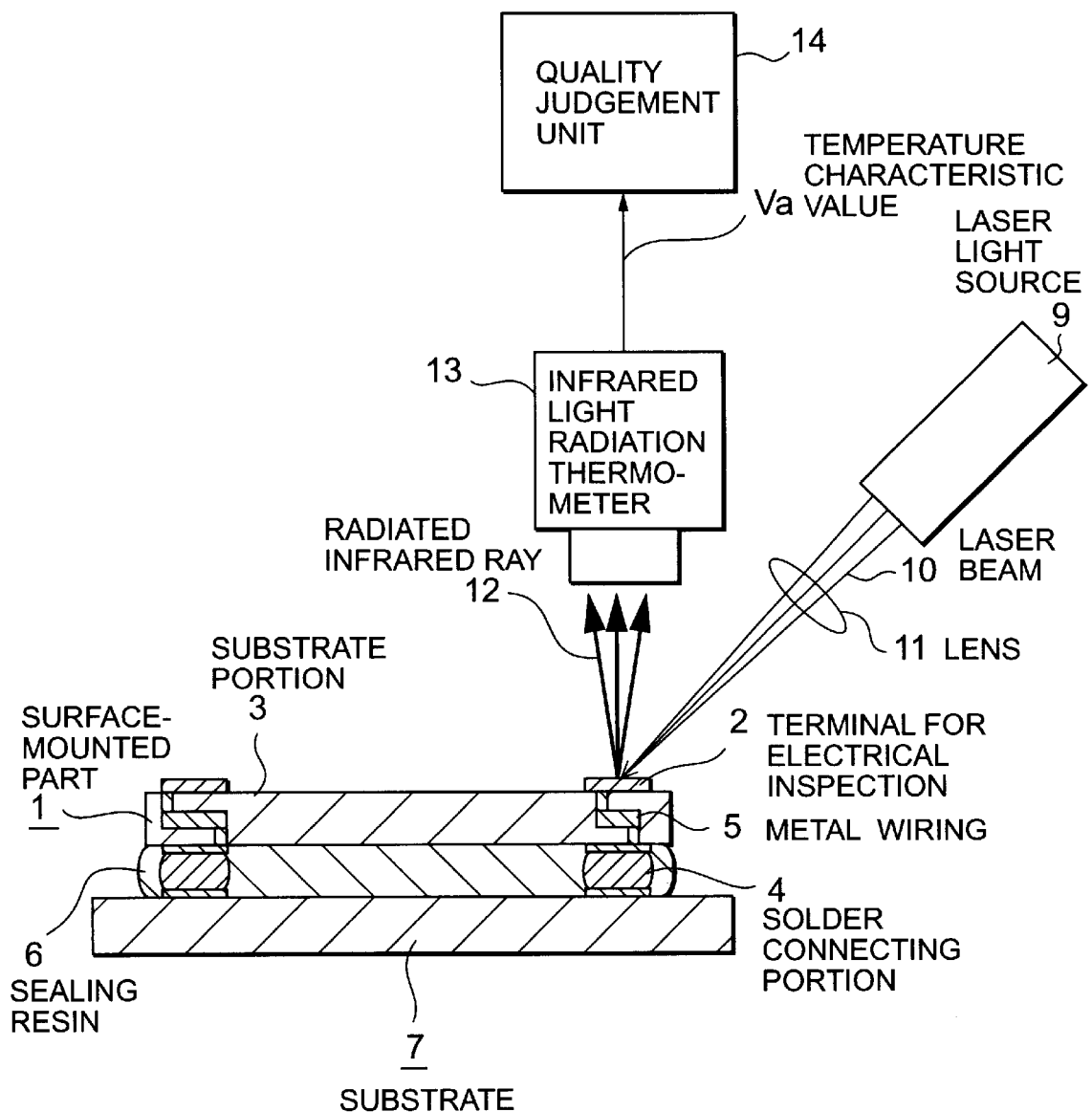
FIG. 1 is a front cross-sectional view of a connection state inspecting apparatus for an electronic part and a substrate in the first embodiment of the present invention.

FIG. 1 is a front cross-sectional view of a connection state inspecting apparatus for an electronic part and a substrate in the first embodiment of the present invention. The apparatus shown in FIG. 1 has a laser light source 9, a lens 11, an infrared light radiation thermometer 13 and a quality judgement unit 14.

A surface-mounted part 1, which is the part to be checked by this apparatus, has terminals for electrical inspection 2, a substrate portion 3, solder connecting portions 4 and metal wiring 5.

The substrate portion 3 consists of silicon or ceramic, mounted with silicon integrated circuits (not shown) and the like.

The solder connecting portions 4 consist of bumps and the like formed on the bottom surface of the substrate portion 3.

The terminals for electrical inspection 2 consist of metal pads and the like formed on the top surface of the substrate portion 3. The terminals 2 are connected to silicon integrated circuits (not shown) and the like built into the surface-mounted part 1, and provided to measure the electrical characteristics of this surface-mounted part 1.

The metal wiring 5, formed within the substrate portion 3, connects the solder connecting portions 4 and the terminals for electrical inspection 2 to each other.

Further, the space between the surface-mounted part 1 and a substrate 7 is filled with sealing resin 6.

In the apparatus shown in FIG. 1, the laser light source 9 is the heating light source for emitting the laser beam 10.

The lens 11, disposed on the optical axis of the laser beam 10 radiated from the laser light source 9, is a beam condensing optical element for condensing the laser beam 10 into a diameter not larger than the external diameter of the terminals 2 on their surface.

The infrared light radiation thermometer 13 is a thermometer for receiving the radiated infrared ray 12 emitted from the terminals 2 themselves by their temperature rise. The thermometer 13 supplies temperature character value Va representing a degree of temperature corresponding with the intensity of the radiated infrared ray 12.

Figure 3:
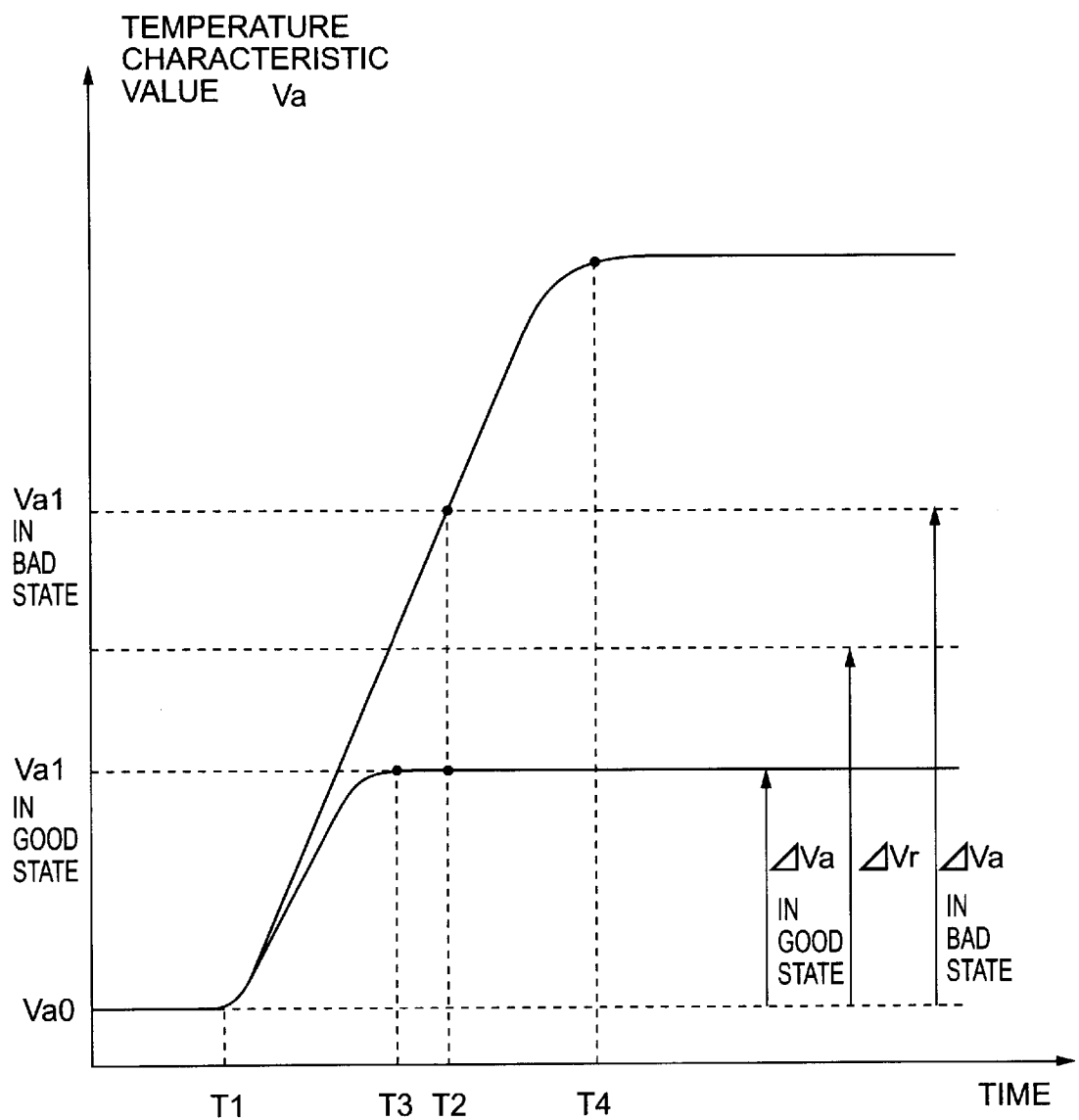
FIG. 3 is a diagram of temperature-time relations on the heated positions of the electronic part according to the FIG. 1 embodiment.

The quality judgement unit 14 is a means for judging the quality of the connection state of either the solder connecting portions 4 or the metal wiring 5. The quality judgement unit 14 calculates the difference between the temperature character value Va0 (FIG. 3) before irradiation with the laser beam 10 and the temperature character value Va1 (FIG. 3) at a certain point of time after the start of irradiation as a temperature character increment $\Delta Va$ (=Va1−Va0) (FIG. 3). The quality judgement unit 14 compares it with a threshold of the temperature character increment $\Delta Vr$ (FIG. 3) stored within in advance. The quality judgement unit 14 here will judge the connection state to be bad if the temperature character increment $\Delta Va$ surpasses the threshold of the temperature character increment $\Delta Vr$. The temperature character increment $\Delta Vr$ is as a reference value of the quality judgement.

Next will be explained the principle of judgement.

The laser beam 10 emitted from the laser light source 9 is condensed by the lens 11 to a diameter not larger than the external diameter of the terminals 2, and irradiates the terminals 2. Only a part of the irradiating laser beam 10 undergoes heat absorption by the terminals 2 to raise the temperature of the terminals 2.

When the temperature of the terminals 2 rises, there occurs a temperature difference from the substrate portion 3 and other elements around them, resulting in a heat flow diffusing around. The temperature of terminals 2 rises with the lapse of time. As the quantity of the heat flow here diffusing from the terminals 2 to the substrate portion 3 and other elements around them is proportional to the temperature difference. When the quantity of heat absorbed from the laser beam 10 and the quantity of diffusing heat become equal, the temperature rise of the terminals 2 becomes saturated.

Now, there is a thermal resistance R between the terminals 2 and the substrate portion 3 and other elements around. The thermal resistance R can be represented by $R=(\Delta T/Q)$, where Q is the quantity of heat flow at a temperature difference $\Delta T$. Thus if the temperature difference $\Delta T$ is constant, the greater the thermal resistance R, the smaller the heat flow quantity Q.

The thermal resistance R of an object having a thermal conductivity $\lambda$, a size of cross section A and a length L is represented by $R=\{L/(\lambda A)\}$.

Further, the thermal resistance R in convective heat conduction to the surrounding air can be represented by $R=\{1/(\alpha A)\}$, where $\alpha$ is the thermal conductivity.

Figure 2:
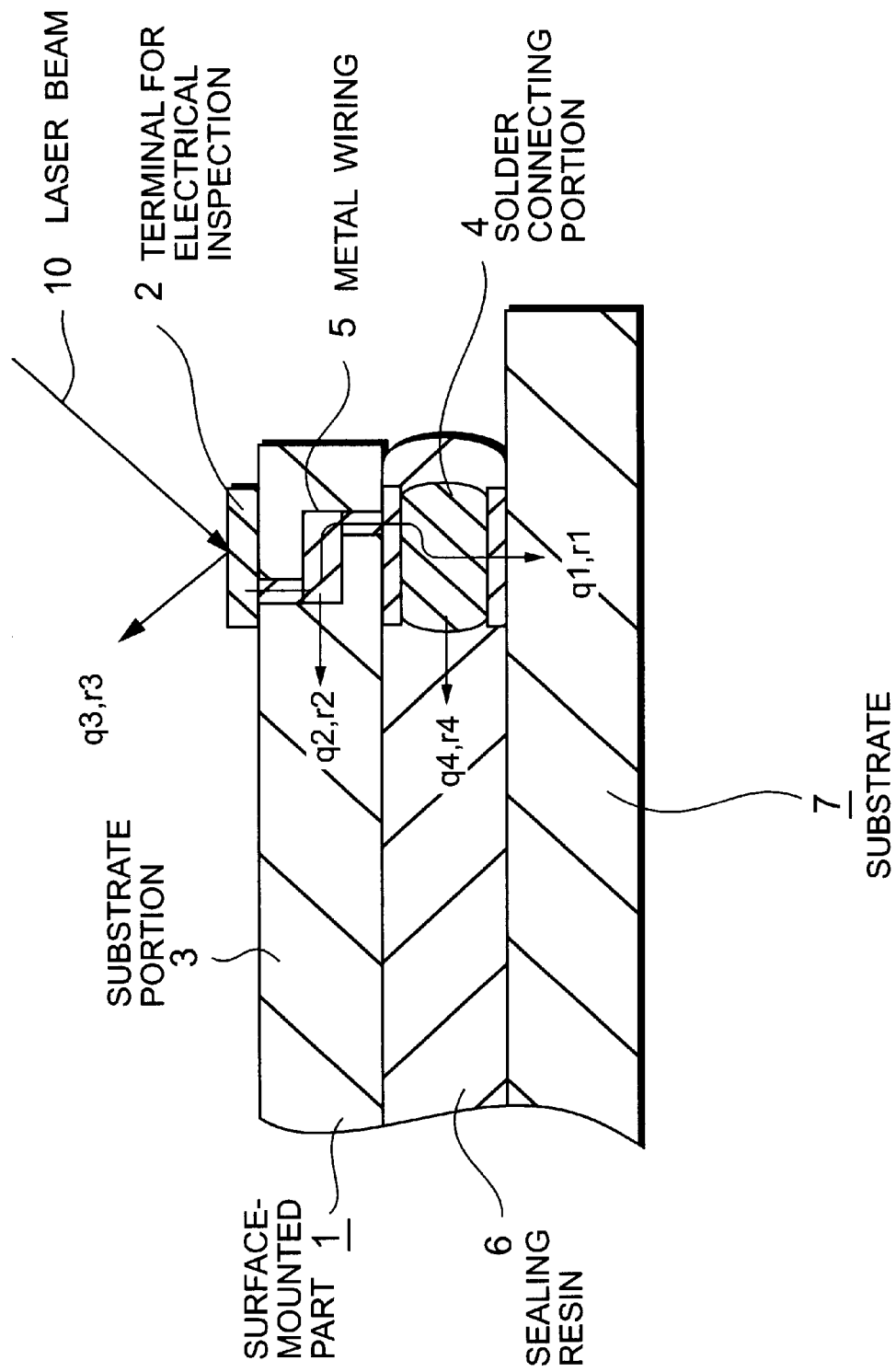
FIG. 2 is an enlarged partial front cross-sectional view of the electronic part and the substrate showing heat flow according to the FIG. 1 embodiment.

FIG. 2 is an enlarged partial front cross-sectional view of the electronic part and the substrate showing heat flow according to the FIG. 1 embodiment. As shown in FIG. 2, there are four kinds each of heat flow quantity and thermal resistance:

(1) A heat flow quantity q1 and a thermal resistance r1 to the substrate 7 thermally coupled by the metal wiring 5 and the solder connecting portions 4;

(2) A heat flow quantity q2 and a thermal resistance r2 to the substrate portion 3;

(3) A heat flow quantity q3 and a thermal resistance r3 of convective heat conduction from the surface of the terminals 2 to the air around them; and (4) A heat flow quantity q4 and a thermal resistance r4 from the surface of the solder connecting portions 4 to the sealing resin 6 around them.

Here, when the temperature rise is saturated, the following equation holds:

$$Q_0 = (q_1+q_2+q_3+q_4) = \{(T0-T1)/(r1+r2+r3+r4)\}$$

where Q0 is the heat intake from the laser beam 10; T0, the temperature of the terminals 2; T1, the temperature around the terminals 2 when heat diffuses from the terminals 2.

The heat flow quantities and the thermal resistances of (1) through (4) above are constant, irrespective of the quality of the connection state of the solder connecting portions 4. Therefore, the thermal resistance r1 varies with the quality of the connection state of the solder connecting portions 4 or of the metal wiring 5, so that the saturation temperature T0 varies.

If the connection state of the solder connecting portions 4 and the metal wiring 5 is good, i.e. if there is no such abnormality as disconnection or crack in the solder connecting portions 4 and the metal wiring 5, the thermal resistance r1 to the substrate 7 will be small. This results in that the saturation temperature T0 will be low.

If the connection state of the solder connecting portions 4 or the metal wiring 5 is wholly bad, i.e. if there is any complete break on the way in the solder connecting portions 4 or the metal wiring 5, there will be an air layer intervening in the break, resulting in a far greater thermal resistance r1 than in a good state. This results in that the saturation temperature T0 will be very high.

In a bad state wherein the solder connecting portions 4 or the metal wiring 5 is only partly connected, i.e. where a crack or the like has arisen, the cross section of the heat flow will shrink, resulting in a greater thermal resistance r1 than in a good state. This results in that the saturation temperature T0 will be high.

The present invention makes possible accurate judgement of the quality of the connection state of the solder connecting portions 4 or the metal wiring 5 by measuring the saturation temperature T0, or the characteristic of the temperature rise until saturation, in accordance with such a principle.

Then, the temperature character value Va representing the intensity of the radiated infrared ray 12 radiated from the terminals 2 themselves due to their temperature rise is measured by the infrared light radiation thermometer 13. The connection state of the solder connecting portions 4 and metal wiring 5 is measured by the quality judgement unit 14 on the basis of the temperature character increment ΔVa, which is the increment of the temperature character value Va.

FIG. 3 is a diagram of the temperature-time relations on the heated positions of the electronic part according to the FIG. 1 embodiment.

First, the quality judgement unit 14 calculates the difference between the temperature character value Va0 before irradiation with the laser beam 10 (T1) and the temperature character value Va1 at a certain point of time after the start of irradiation (T2) as a temperature character increment ΔVa (=Va1−Va0). Here, it is only necessary a sufficient time for accurate judgement of the connection state. This sufficient time is, at least, from the start of radiation of the laser beam 10 to the saturation of the temperature in a good state (T3) and a temperature character value Va sufficiently above the threshold of the temperature character increment ΔVr. Namely, there will be no need to wait until the temperature rise becomes saturated (T4).

Next, this temperature character increment ΔVa is compared with the threshold of the temperature character increment ΔVr. This temperature character increment ΔVa varies from one terminal 2 to another, because the metal wiring 5 within the surface-mounted part 1 differs in shape and length from one terminal to another. The thermal resistance and thermal capacity from each of the terminals 2 to each of the solder connecting portions 4 differ each other.

Then each inherent threshold of the temperature character increment ΔVr of each terminal 2 is determined, and stored into an internal memory or the like in the quality judgement unit 14 in advance.

What is used as this threshold of the temperature character increment threshold αVr is a threshold between a temperature character increment αVa in a good state and a temperature character increment αVa in a bad state. These temperature character increments αVa are obtained by irradiating with a laser beam 10 of a specific intensity on the same positions on terminals 2 in a large number of samples of the surface-mounted part 1. These samples of the surface-mounted part 1, having the same structure and the same wiring pattern as the part to be inspected, includes both good and bad ones in terms of the connection states, by similarly soldering each of the surface-mounted part 1 onto a substrate 7.

The quality judgement unit 14 compares these threshold of the temperature character increment αVr and temperature character increment αVa to judge the quality of the connection state of the solder connecting portions 4 and the metal wiring 5. As the saturation temperature of the terminals 2 is higher when the connection state is bad than when it is good, the quality judgement unit 14 judges that the connection state is bad when the temperature character increment ΔVa surpasses the threshold of the temperature character increment ΔVr.

Further, as thermal resistance and thermal capacity vary from one terminal 2 to another, instead of compensating the threshold of the temperature character increment ΔVr in response to each of the terminals 2, it is also acceptable to store in advance a single temperature character increment ΔVA which would serve as the reference. In this case, the quality judgement unit 14 compensates the single temperature character increment ΔVa according to the differences in thermal resistance and thermal capacity between each of the terminal 2 to serve as the reference and each of the terminals 2 to be measured. The quality judgement unit 14 compares the compensated temperature character increment ΔVA and the single threshold of the temperature character increment ΔVr.

Then, for the laser beam 10, one having a wavelength with a high absorptive character at the terminals 2 is chosen.

For this embodiment, the YAG (yttrium-aluminum-garnet) laser beam of 1064 nm in wavelength or the $CO_2$ laser beam of 10600 nm in wavelength, both used for the conventional example, are unsuitable because they are highly reflected but hardly absorbed by the gold plated layer on the surface of the terminals 2.

Moreover, the YAG laser beam and the $CO_2$ laser beam belong to the near infrared to the infrared regions are within the measurable wavelength range of the infrared light radiation thermometer 13. If either of them irradiates the gold plated layer in a high output, it will be scattered by the highly reflective surface of the gold plated layer, resulting in a very high intensity of the scattered light invading the thermometer 13. This brings down the accuracy of temperature measurement by the thermometer 13.

Therefore, as the laser beam 10 for use in this embodiment, a short wavelength laser beam such as Ar laser beam of 488 nm in wavelength, or the second harmonic of the YAG laser beam of 532 nm in wavelength or that of $YVO_4$ laser beam, is suitable because it is less reflected by the gold plated layer and is outside the measurable wavelength range of the thermometer 13.

Thus in this embodiment, the existing terminals for electrical inspection, formed in advance at the time of fabricating electronic parts for the purpose of facilitating electrical continuity inspection, are irradiated with the laser beam.

Furthermore, as the temperature character increment ΔVa measured by this irradiation is compared with the threshold of the temperature character increment ΔVr as the reference to judge the quality of the connection state, the connection state of electronic parts can be accurately evaluated without having to add such structural elements as through holes and pads for the sole purpose temperature measurement.

Second Embodiment

Figure 4:
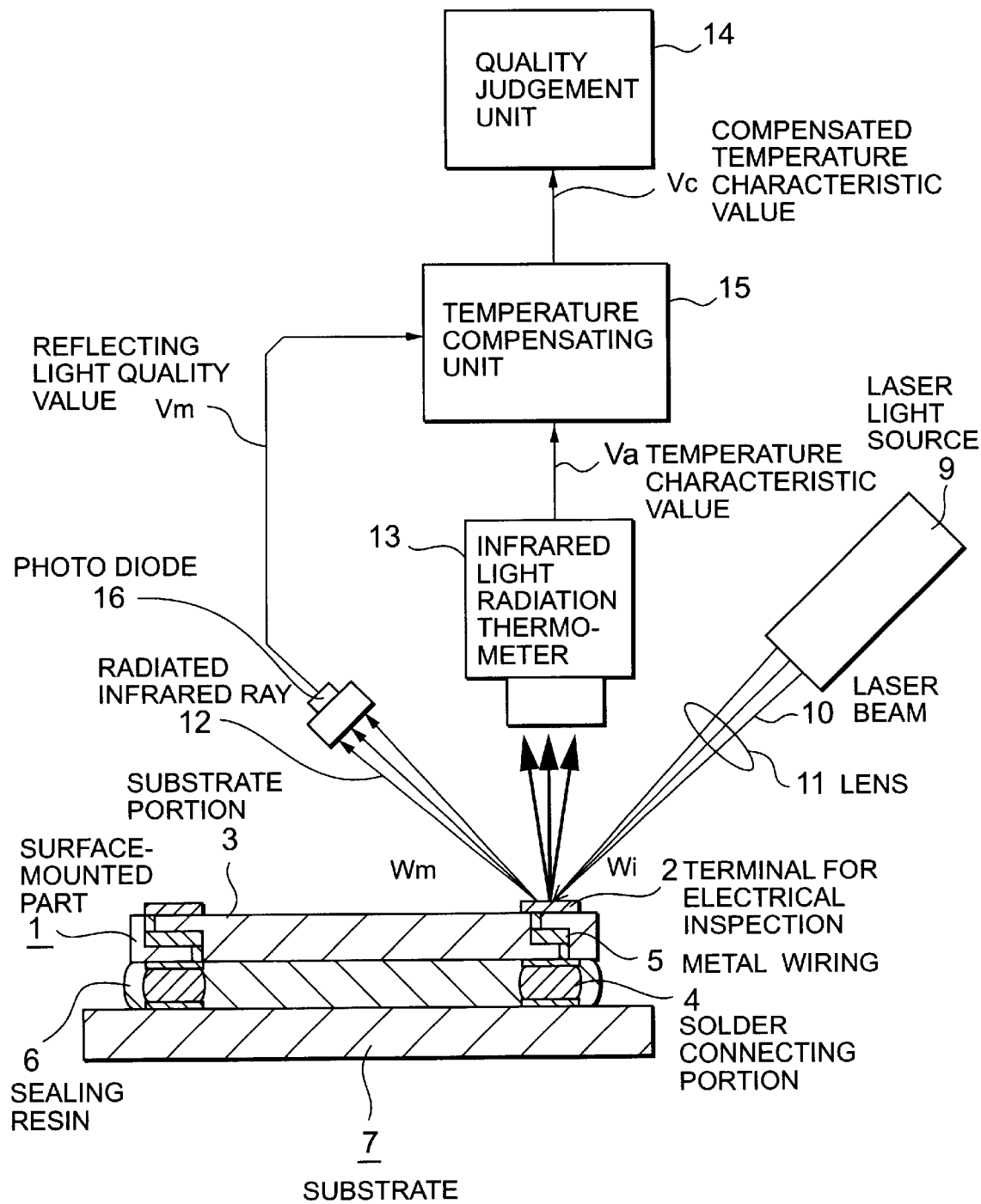
FIG. 4 is a front cross-sectional view of a connection state inspecting apparatus for an electronic part and a substrate in the second embodiment of the present invention.

FIG. 4 is a front cross-sectional view of a connection state inspecting apparatus for an electronic part and a substrate in the second embodiment of the present invention. Adding a temperature compensating unit 15 and a photo diode 16 to the apparatus of FIG. 1 configures the apparatus shown in FIG. 4.

The photo diode 16 is disposed on a position where the laser beam 10 irradiating the terminals for electrical inspection 2 is regularly reflected. The photo diode 16 measures reflected luminous energy Wm of the laser beam 10 regularly reflected by the surfaces of the terminals 2, and outputs as a measured reflected luminous energy value Vm.

The temperature compensating unit 15, on the basis of the reflected luminous energy value Vm from the photo diode 16, compensates the temperature character value Va from the infrared light radiation thermometer 13 and outputs the resultant compensated temperature character value Vc.

The quality judgement unit 14, on the basis of the compensated temperature character value Vc, judges the quality of the connection state of the solder connecting portions 4 and the metal wiring 5.

Next will be explained the principle of judgement. The aspects of processing other than temperature compensation are the same as in the first embodiment, and therefore their description is abbreviated.

First, as in the embodiment of FIG. 1, the terminals 2 are irradiated with the laser beam 10, and the temperature character value Va of the terminals 2 is thereby measured.

At the same time, the photo diode 16 measures the reflected luminous energy Wm of the laser beam 10 regularly reflected by the surface of the terminals 2, and outputs the resultant reflected luminous energy value Vm.

Next, the temperature compensating unit 15 compensates the measured temperature character value Va on the basis of the reflected luminous energy value Vm from the photo diode 16, an emitted luminous energy Wi of the laser light source 9 preset within the temperature compensating unit 15, and an ideal per-second heating quantity Q. The temperature compensating unit 15 supplies the resultant compensated temperature character value Vc to the quality judgement unit 14.

When the surface of the terminals 2 is flat and smooth and the reflected light therefrom contain nothing else than the regularly reflected light, this temperature compensating unit 15 assumes that the luminous energy of the difference between the emitted luminous energy Wi and the reflected luminous energy Wm has been absorbed by the terminals 2. The temperature compensating unit 15 calculates the per-second heating quantity Qm as the equation that Qm=Wi−Wm.

Further the temperature compensating unit 15 calculates the compensated temperature character increment ΔVc (=ΔVa×Q/Qm) on the basis of the ideal per-second heating quantity Q preset therein and a measured temperature character increment Δva (=Va1−Va0).

This ideal per-second heating quantity Q is calculated in advance as a per-second heating quantity Q (=Wi−Wr) from the reflected luminous energy Wr of the clean surface of the terminals 2, free from smear.

Or if the surface of the terminals 2 has fine irregularities inviting scattered light besides the regularly reflected light, the reflected luminous energy Wm measured by the photo diode 16 contains only a part of the luminous energy reflected by the terminals 2. The ratio between the reflected luminous energy Wm measured by the photo diode 16 and the total reflected luminous energy including the regularly reflected luminous energy reflected by the terminals 2 and the scattered light is figured out in advance. The multiplication of the measured compensated temperature character increment ΔVc by the invert of this ratio will give the actual compensated temperature character increment ΔVc.

Thus this embodiment, even where the surface of the terminals for electrical inspection is smeared, inviting fluctuation of the quantity of absorbed heat, can judge the quality of the connection state even more accurately than the first embodiment because the measured temperature is compensated according to the reflected luminous energy.

Third Embodiment

Figure 5:
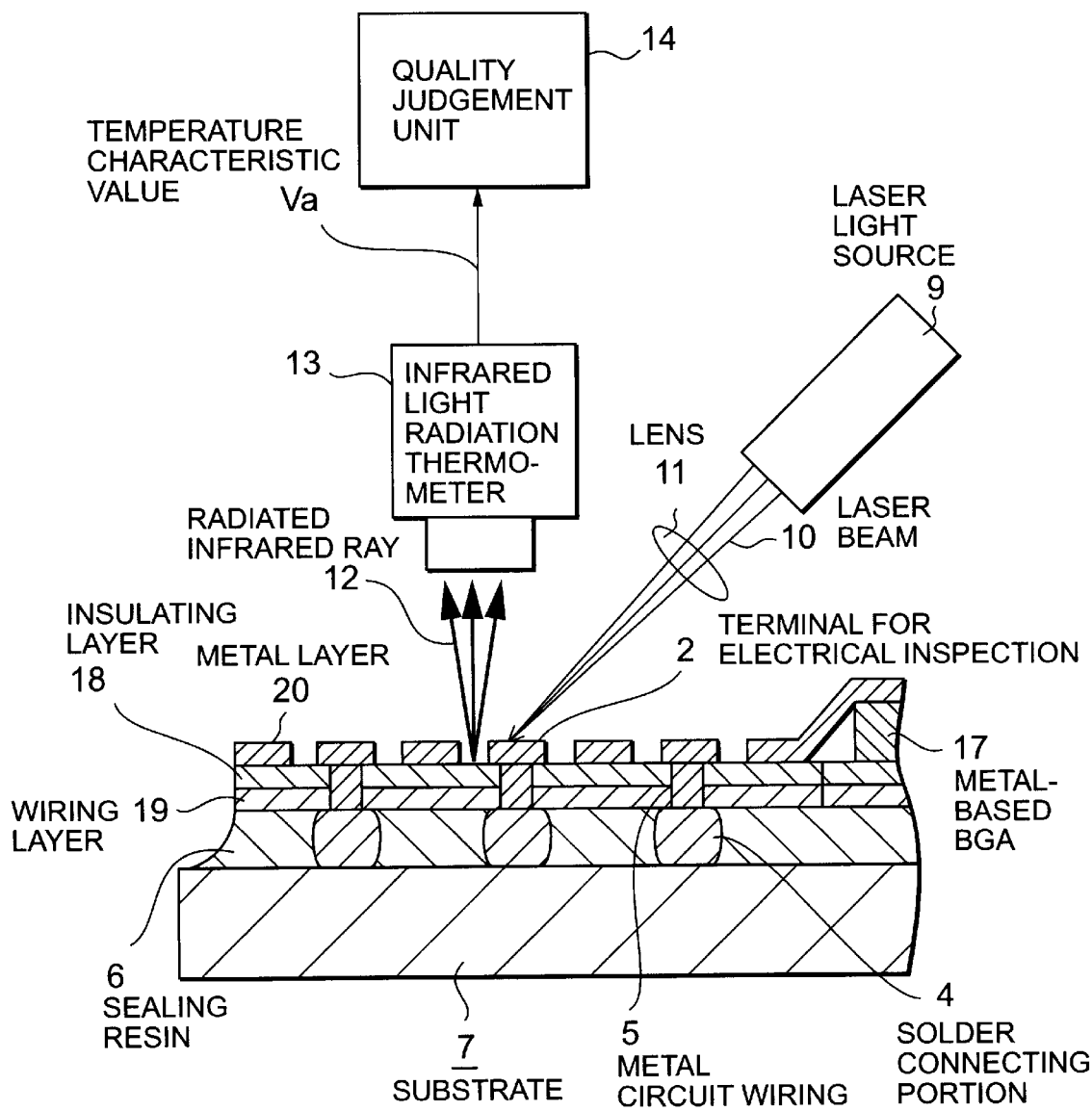
FIG. 5 is a front cross-sectional view of a connection state inspecting apparatus for an electronic part and a substrate in the third embodiment of the present invention.

FIG. 5 is a front cross-sectional view of a connection state inspecting apparatus for an electronic part and a substrate in the third embodiment of the present invention. The apparatus shown in FIG. 5 has a configuration similar to that of the embodiment shown in FIG. 1.

A metal-based ball grid array (hereinafter abbreviated as metal-based BGA) 17 shown in FIG. 5, which is the part to be checked, is a sort of surface-mounted part having a rectangular planar shape and consisting of silicon, ceramic or a similar material. It is mounted with silicon integrated circuit elements and the like (not shown), and the terminals for electrical inspection 2, for use in electrical continuity inspection, and metal layers 20 for radiating heat are formed over its surface.

This metal-based BGA 17 is connected to a substrate 7 by the solder connecting portions 4 consisting of solder bumps or the like, and the terminals 2 and the solder connecting portions 4 are connected to each other by the metal circuit wiring 5.

In the lower part of the terminals 2 is provided an insulating layer 18 to insulate the terminals 2, the metal layer 20 and a wiring layer 19 from one another.

The gap between the metal-based BGA 17 and the substrate 7 is filled with sealing resin 6.

Next will be explained the principle of judgement.

The laser beam 10 from the laser light source 9 irradiates onto the terminals 2. The intensity of the radiated infrared rays 12 of intensity corresponds to the heat applied to the terminals 2.

If the surface of the terminals 2 here is plated with gold, the intensity of the radiated infrared rays 12 from the terminals 2 will be too low because the infrared emission character of gold is very low, preventing the terminals 2 from measuring the temperature rise accurately.

In view of this problem, in this embodiment, the terminals 2 are replaced as temperature measuring positions by the insulating layer 18 around the terminals 2, and the radiated infrared ray 12 emitted from the insulating layer 18 is measured with the infrared light radiation thermometer 13. This insulating layer 18 has a higher infrared radiation character than the terminals 2, and the heat conducted from the terminals 2 has a sufficient temperature rise.

The quality judgement unit 14 compares the temperature character increment $\Delta VA$ calculated by the temperature character value Va from the thermometer 13 with the threshold of the temperature character increment $\Delta Vr$ to judge the quality of the connection state of the solder connecting portions 4 and the metal circuit wiring 5. Here the connection state is judged to be bad if the temperature character increment $\Delta VA$ surpasses the threshold of the temperature character increment $\Delta vr$.

Thus in this embodiment, even though the part to be checked is the metal-based BGA, with the surface of the terminals for electrical inspection being plated with gold, highly accurate judgement is made possible on the basis of radiated infrared rays from the insulating layer exposed around the terminals.

Fourth Embodiment

Figure 6:
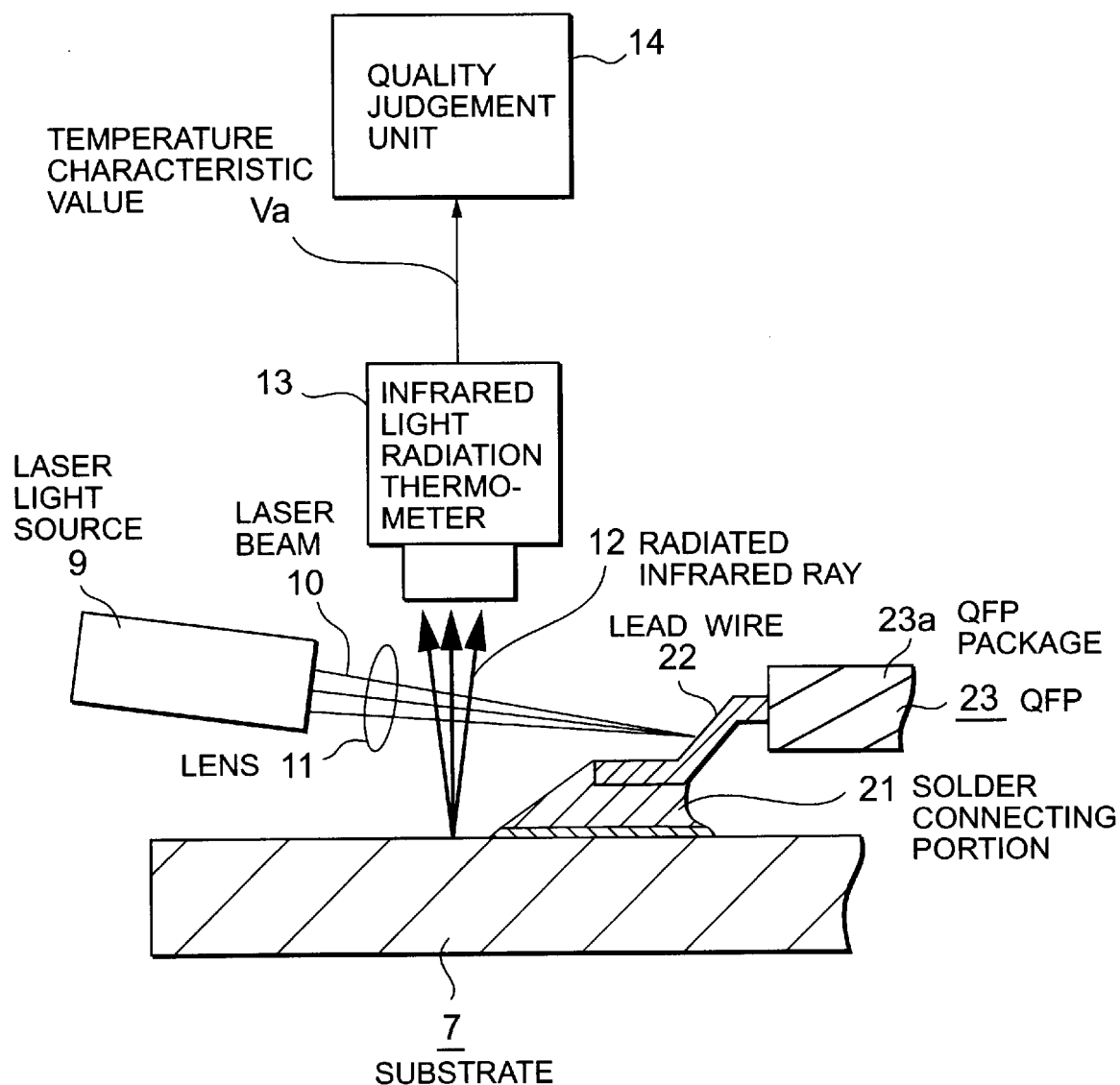
FIG. 6 is a front cross-sectional view of a connection state inspecting apparatus for an electronic part and a substrate in the fourth embodiment of the present invention.

FIG. 6 is a front cross-sectional view of a connection state inspecting apparatus for an electronic part and a substrate in the fourth embodiment of the present invention. The apparatus shown in FIG. 6 has a configuration similar to that of the embodiment shown in FIG. 1.

A quad flat package (hereinafter abbreviated as QFP) 23 shown in FIG. 6, which is the part to be checked, is a sort of surface-mounted part having a rectangular planar shape and consisting of silicon, ceramic or a similar material. It is mounted with silicon integrated circuit elements and the like (not shown), and consists of a QFP package 23a and lead wires 22 radially disposed on the edges of this QFP package 23a toward the surrounding areas.

Next will be explained the principle of judgement.

The laser beam 10 from the laser light source 9 is condensed by the lens 11 and irradiates the lead wires 22. A part of the irradiating laser beam 10 is absorbed by the lead wires 22 to raise their temperature.

As the temperature of the lead wires 22 rises, there arises a temperature difference in the substrate 7 connected to the lead wires 22 by the solder connecting portions 21 and other surrounding parts, and consequently a heat flow is generated. The quantity of this heat flow, as its counterpart in the first embodiment, varies with the thermal resistance and thermal capacity of the solder connecting portions 21. When the connection state of the solder connecting portions 21 is bad, the temperature of the lead wires 22 is higher than when it is good, and the temperature around the solder connecting portions 21 over the substrate 7 drops.

The quality judgement unit 14, on the basis of the temperature character value Va from the thermometer 13, judges the quality of the connection state of the solder connecting portions 21. Since all the lead wires 22 here are identically shaped, the thermal resistances and thermal capacities of the lead wires 22 can be assumed to be exactly equal.

Then, this embodiment judges the quality of the connection state of each solder connecting portion 21 with reference to a unitary common threshold of the temperature character increment $\Delta Vr$ of the lead wires 22. Here, the temperature rise of the substrate 7, which is the destination of heat transmission, is measured. Therefore, when the temperature character increment $\Delta VA$ is less than the threshold of the temperature character increment $\Delta Vr$, the connection state is judged to be bad.

This embodiment, as it judges the quality of the connection state by measuring the substrate 7, which is the destination of heat transmission, is suitable for use where the lead wires 22 are thin and the heat flow quantity is small.

The reason is that, where the heat flow quantity is small, the heat absorbed by the lead wires 22 is transmitted to the substrate 7, and accordingly there is almost no difference in the temperature rise of the lead wires 22 whether the connection state is good or bad.

For instance, where the heat flow quantity available to raise the temperature of the lead wires 22 is 90% of the total heat quantity in a good state or 95% of the same in a bad state, the temperature in the bad state is only about 1.1 (=95/90) times as high as in the good state. It would be very difficult to judge the quality of the connection state according to the temperature rise of the lead wires 22.

By contrast, the heat flow quantity transmitted to the solder connecting portions 21 is about 10% (=100%–90%) of the total heat quantity in the good state and 5% (=100%–95%) of the same in the bad state, so that the temperature in the bad state is about 2 (=10/5) times as much as that in the good state. The quality judgement according to the temperature of the solder connecting portions 21 or the substrate 7 can be highly precise.

Thus this embodiment can judge the connection state exactly and very precisely even where the heat flow quantity from the part to be checked to the solder connecting portions is small, because the temperature rise of the substrate, which is the destination of heat transmission, near the solder connecting portions is measured for the judging purpose.

Fifth Embodiment

Figure 7:
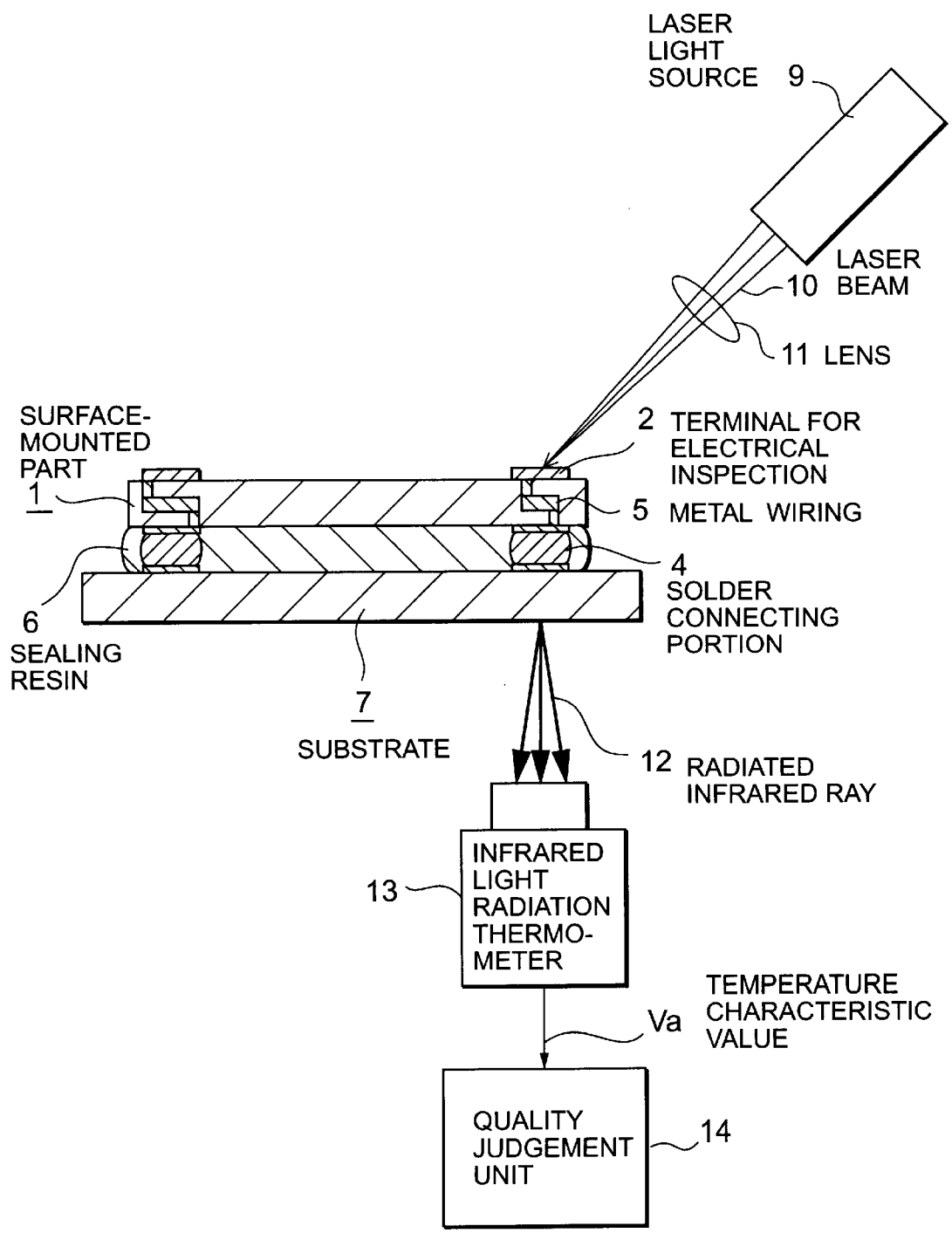
FIG. 7 is a front cross-sectional view of a connection state inspecting apparatus for an electronic part and a substrate in the fifth embodiment of the present invention.

FIG. 7 is a front cross-sectional view of a connection state inspecting apparatus for an electronic part and a substrate in the fifth embodiment of the present invention. The apparatus shown in FIG. 7 has a basically similar configuration to that of the apparatus of FIG. 1, and only the differences will be explained below.

As shown in FIG. 7, the infrared light radiation thermometer 13 is arranged on the other side of the laser light source 9 with the substrate 7 in-between. The thermometer 13 receives radiated infrared rays 12 from the backside of the substrate 7 disposed immediately underneath the solder connecting portions 4 and having a high infrared radiation character, and outputs a temperature character value Va.

The quality judgement unit 14 judges the connection state of the solder connecting portions 4 on the basis of the temperature character value Va from the infrared light radiation thermometer 13.

This embodiment judges the connection state of the solder connecting portions 4 with reference to the threshold of the temperature character increment $\Delta Vr$ which is unique to each terminal 2. Here, the temperature rise of the substrate 7, which is the destination of heat transmission, is measured. Therefore, when the temperature character increment $\Delta VA$ is less than the threshold of the temperature character increment $\Delta Vr$, the connecting state is judged to be bad.

Thus this embodiment can judge exactly and accurately the connection state of the part to be checked in which the temperature measuring positions having a high infrared radiation character. Accordingly, it is suitable for the electrical part having no position for measuring temperature rise over the substrate or having a thin substrate.

Sixth Embodiment

Figure 8:
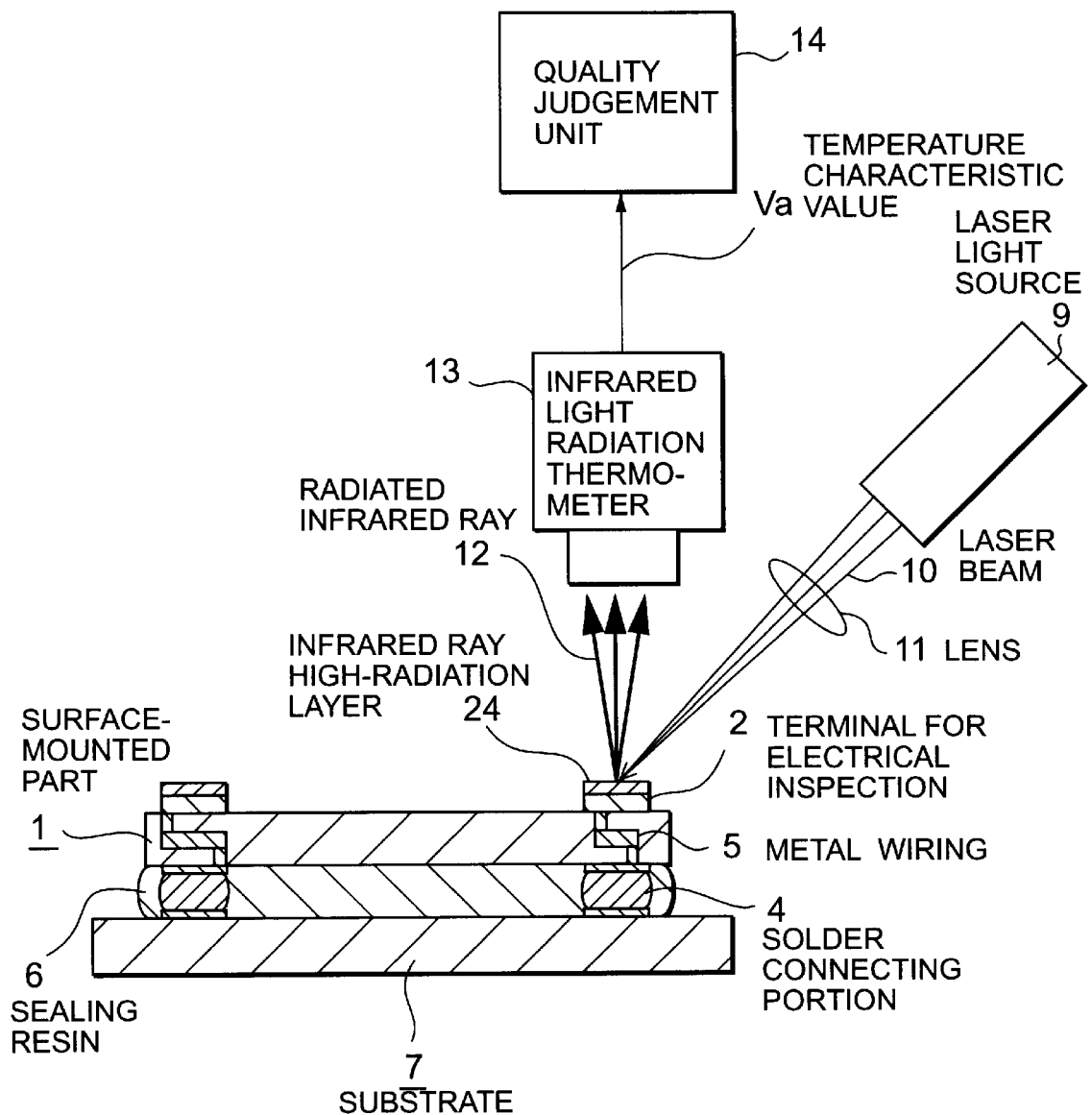
FIG. 8 is a front cross-sectional view of a connection state inspecting apparatus for an electronic part and a substrate in the sixth embodiment of the present invention.

FIG. 8 is a front cross-sectional view of a connection state inspecting apparatus for an electronic part and a substrate in the sixth embodiment of the present invention. The apparatus shown in FIG. 8 differs from the connection state inspecting apparatus of FIG. 1 in that an infrared ray high-radiation layer 24 is formed over each of the surface of the terminals for electrical inspection 2, which is the part to be checked, and is the same in other aspects of the configuration.

The layer 24 is formed by coating the surface of the terminals 2 with paint having a high infrared radiation character or otherwise. Examples of such paint include a black heat-resistant paint available from Asahi Paint Co., Ltd. of Japan, having an infrared radiation rate of 0.98.

The method to form this layer 24 is not limited to coating with the paint. For instance, if a plating material with a high infrared radiation character is available, plating will be a reasonable alternative. or else, as a rugged surface would give a higher infrared radiation character than a smooth surface even if the material is the same, fine irregularities may be formed on the surface of the terminals 2. In other words, any way of surface treatment of the terminals 2 will be acceptable if it can enhance the infrared radiation character of the terminals 2.

Since in this embodiment the light absorption character and the infrared radiation character of the 2 are enhanced, the laser light source 9 needs no high optical output.

Alternatively, instead of forming the layer 24 over the surface of the terminals 2, the layer 24 may be formed near the terminals 2, and the temperature of this layer 24 may be measured. This alternative is applicable where it is desired to expose the surface of the terminals 2 to bring into contact a probe or the like during electrical continuity inspection and there is no position of a high infrared radiation character near the terminals 2.

Thus this embodiment permits exact and highly accurate judgement of the connection state where the part to be checked has no position of a high infrared radiation character near the position of heating, near the solder connecting portions over the substrate or on the back side of the substrate.

The threshold of the temperature character increment ΔVr of a different value is used for each position of inspection in the first, third, firth and sixth embodiments of the invention because the thermal resistance and thermal capacity of the metal wiring 5 connected thereto differs from one position to another. If the cross sections and lengths of the metal wiring 5 are the same in every position of inspection, the thermal resistances and thermal capacities can be assumed to be the same in all the position, and a unitary threshold of the temperature character increment ΔVr can be used.

In any of the above-described embodiments, it is not required to know accurately the absolute temperature of the part to be checked, because the quality of the connection state can be judged only based on the temperature rise of the part to be checked differs between a good state and a bad state. Therefore, any judgement method can be applied to any of the above-described embodiments. For instance, if the temperatures T0 of a plurality of terminals 2 before irradiation with the laser beam 10 are constant in every measurement, the temperature T0 before irradiation with the laser beam 10 need not be measured.

Further, any other suitable temperature measuring means than the infrared light radiation thermometer 13 may be used. For instance, a thermocouple device with an extremely small thermal capacity and a sensitive response to temperature may be used by contacting on the terminals 2.

As hitherto described, the present invention is no need to newly add a structure for temperature measurement to any electronic part, because the terminals for electrical inspection already provided in the part to be checked can be utilized as they are. This results in substantial economies in the designing process and the manufacturing process while making possible highly accurate evaluation of the connection state of the solder connecting portions and the wiring route.

Furthermore, if the temperature is measured on a position having a high infrared radiation character, thermally coupled to the position of heating, the accuracy of judgement can be enhanced even further.

What is claimed is:

1. A method for inspecting a connection state of an electronic part and a substrate, said electronic part having a solder portion connected on a major surface of said substrate, a terminal for electrical inspection, and a wiring electrically connecting between said solder portion and said terminal, said method comprising the steps of:

calculating beforehand a thermal resistance of said wiring and estimating a reference temperature rise of said terminal by using said calculated thermal resistance;

heating said terminal by irradiating a laser beam on said terminal;

measuring a temperature rise of said terminal; and judging a quality of a connection state of said solder portion by said measured temperature rise and said reference temperature rise of said terminal.

2. A method for inspecting a connection state of an electronic part and a substrate of claim 1 wherein said reference temperature rise is a threshold between a temperature rise in a good connection state and a temperature rise in a bad connection state.

3. A method for inspecting a connection state of an electronic part and a substrate of claim 1 wherein said laser beam is of an Ar laser, a second harmonic of YAG laser or a $YVO_4$ laser.

4. A method for inspecting a connection state of an electronic part and a substrate of claim 1 wherein said electronic part includes a metal based ball grid array.

5. A method for inspecting a connection state of an electronic part and a substrate of claim 1 wherein said wiring has a horizontal part extending in parallel with said major surface of said substrate.

* * * * *